(12) United States Patent
McMichael et al.

(10) Patent No.: US 8,142,418 B2
(45) Date of Patent: Mar. 27, 2012

(54) AUTOMATIC SHUT-OFF CONNECTOR FOR ENTERAL FEEDING DEVICES

(75) Inventors: Donald J. McMichael, Roswell, GA (US); Nathan Griffith, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 487 days.

(21) Appl. No.: 11/960,052

(22) Filed: Dec. 19, 2007

(65) Prior Publication Data

US 2009/0163892 A1    Jun. 25, 2009

(51) Int. Cl.
*A61M 25/16*    (2006.01)
*A61M 25/18*    (2006.01)

(52) U.S. Cl. ........ 604/537; 604/246; 604/247; 604/256; 604/533; 604/535; 604/539

(58) Field of Classification Search ............... 604/246, 604/247, 249, 256, 523, 533, 534, 535, 536, 604/537, 538, 539, 905
See application file for complete search history.

(56) References Cited

U.S. PATENT DOCUMENTS

| | | | |
|---|---|---|---|
| 3,707,972 A | 1/1973 | Villari et al. | |
| 4,307,903 A | 12/1981 | Wallace | |
| 4,344,435 A | 8/1982 | Aubin | |
| 4,668,217 A * | 5/1987 | Isono | 604/535 |
| 4,826,486 A | 5/1989 | Palsrok et al. | |
| 4,873,977 A | 10/1989 | Avant et al. | |
| 5,098,405 A | 3/1992 | Peterson et al. | |
| 5,344,414 A * | 9/1994 | Lopez et al. | 604/533 |
| 5,403,284 A | 4/1995 | Gross | |
| 5,540,265 A | 7/1996 | Polaschegg | |
| 5,554,140 A | 9/1996 | Michels et al. | |
| 5,713,850 A | 2/1998 | Heilmann et al. | |
| 5,803,509 A | 9/1998 | Adams | |
| 5,836,924 A | 11/1998 | Kelliher et al. | |
| 6,036,171 A * | 3/2000 | Weinheimer et al. | 251/149.1 |
| 6,044,859 A * | 4/2000 | Davis | 137/15.19 |
| 6,045,536 A | 4/2000 | Meier et al. | |
| 6,375,231 B1 | 4/2002 | Picha et al. | |
| 6,682,508 B1 | 1/2004 | Meythaler et al. | |
| 6,808,521 B1 | 10/2004 | McMichael | |
| 6,908,449 B2 | 6/2005 | Willis et al. | |
| 2002/0099360 A1 * | 7/2002 | Bierman | 604/523 |
| 2003/0073971 A1 | 4/2003 | Saker | |
| 2005/0087715 A1 * | 4/2005 | Doyle | 251/149.1 |
| 2005/0090805 A1 | 4/2005 | Shaw et al. | |

FOREIGN PATENT DOCUMENTS

WO    WO 03/024519    3/2003

OTHER PUBLICATIONS

PCT International Search Report, Mar. 12, 2009.

* cited by examiner

*Primary Examiner* — Bhisma Mehta
(74) *Attorney, Agent, or Firm* — Dority & Manning, P.A.

(57) ABSTRACT

An in-line connector for use in an enteral feeding system includes a first component connectable to a first feeding device of the feeding system, and a second component connectable to a second feeding device of the feeding system. A releasable coupling is configured between the first and second components, wherein in a connected state the first and second components define a fluid passage between the different feeding devices. Each of the first and second components includes a one-way automatic shutoff valve configured therein such that in a disconnected state of the components, the shutoff valve in the first component prevents flow out of the first component in a first direction and the shutoff valve in the second component prevents flow out of the second component in a second direction that is opposite from the first direction.

20 Claims, 4 Drawing Sheets

AUTOMATIC SHUT-OFF CONNECTOR FOR ENTERAL FEEDING DEVICES

BACKGROUND OF THE INVENTION

The present invention relates generally to enteral feeding devices, and more particularly to an in-line connector between components of the feeding system.

It is a known medical procedure to catheterize a body in order to provide nutritional solutions directly into the stomach or intestines of a patient. A stoma is formed in the stomach or intestinal wall and a gastrostomy catheter device is placed through the stoma. This device is supplied with a nutritional solution via a tube, adapter, infusion set, or any combination of devices for delivering the nutritional solution for direct injection into a patient's stomach or intestines. This process is referred to as enteral feeding.

To ensure that the gastrostomy device is maintained in the proper position, it is common to use a balloon disposed near the distal (patient) end of a catheter shaft component of the device. Inflating the balloon causes the balloon to contact the anatomical structure (i.e., a duct or stomach wall) and thereby prevent the catheter from moving out of the proper position. Such balloon gastrostomy devices may include a "low-profile" head at the proximal end of the catheter shaft. The head, which also helps hold the balloon catheter in place, includes an opening for receiving the feeding solution and a one-way valve for preventing fluids from passing out of the patient via the catheter. U.S. Pat. Nos. 5,997,503 and 5,997,546 disclose examples of low-profile balloon catheter gastrostomy devices suitable for enteral feeding, and are incorporated by reference herein for all purposes.

An enteral feeding adapter is often used to transfer the solutions from an upstream source to the gastrostomy device, and typically includes an elongate tube having a distal end that engages in the head of the gastrostomy device. This tube typically extends at least partially through the device and maintains the one-way valve in the catheter in an open position during the enteral feeding process. The adapter may be connected directly to a feeding tube or to an infusion set that is, in turn connected to an enteral feeding pump, a drip chamber, or any other mechanism for providing the feeding solution.

A serious problem associated with this configuration and process is that the feeding tube and adapter may accidentally separate during the feeding process and disrupt the flow of nutritional fluids to the patient. In addition, the nutritional solution and any medicine will spill over the patient. The tube connected to the gastrostomy device provides an open pathway to the patient's stomach, and gastric juices will leak out of the tube. These juices can cause burns and other complications.

Solutions to noted problem have been proposed in the art. For example, U.S. Pat. Nos. 5,057,093; 5,322,073; and 5,554,140 describe interlock devices integrally formed with the feeding devices to secure the components together. Clamping devices are also disclosed in U.S. Pat. Nos. 4,230,109 and 5,248,306. U.S. Pat. No. 6,375,231 discloses another proposed solution wherein a clamp secures a feeding adapter in position relative to a feeding device. The clamp includes C-shaped members integrally connected by elastic webs. One of the members attaches to the feeding adapter, and the other member attached to the feeding device. Elastic bands are used to secure the C-shaped members to their respective components.

The present invention provides a novel solution to the problem of separation of in-line components in an enteral feeding system that does not depend on axially clamping separate feeding members together.

SUMMARY

Objects and advantages of the invention will be set forth in part in the following description, or may be obvious from the description, or may be learned through practice of the invention.

The invention will be described in greater detail below by reference to embodiments thereof illustrated in the figures.

An in-line connector is provided for use in an enteral feeding system. The connector is not limited to use with any particular type of enteral feeding system, and may be configured or modified for use as an in-line component with virtually any enteral feeding system. The connector includes a first component that is connectable to a first feeding device of the enteral feeding system, a second component that is connectable to a second device of the feeding system. In this manner, the connector functions as an in-line separable component between the first and second feeding devices of the enteral feeding system.

A releasable coupling is configured between the first and second components. The coupling may be any suitable mechanical coupling that allows the components to be securely connected in an in-line configuration, yet releasable from each other to separate the first and second feeding devices of the enteral feeding system. In a connected state of the first and second components, a fluid passage is defined between the first and second feeding devices.

Each of the first and second components includes an automatic shut-off valve configured therein such that, in a disconnected state of the first and second components, the shut-off valve in the first component prevents flow out of the first component in a first direction, and the shut-off valve in the second valve component prevents flow out of the component in a second direction that is opposite from the first direction. For example, in a particular embodiment of the connector, the first component is mated with an upstream feeding tube or other device that delivers a nutritional solution from a source in a first direction towards a patient, for example to a gastrostomy feeding device in the patient where the nutritional source is delivered directly into the patient's stomach or digestive system. In this embodiment, the second component is mated with a downstream feeding adaptor, or other feeding device, that is in direct communication with the gastrostomy device. In the disconnected state of the connector, the shut-off valve in the second component prevents backflow of the nutritional solution and gastric juices from flowing leaking out onto the patient (or bedding, etc.) even if the one-way valve in the gastrostomy device is open. Accordingly, in the event that the first and second components of the connector become unconnected (intentionally or unintentionally), flow of the nutritional source in the first direction is halted by the automatic shut-off valve in the first component, and reverse flow of the nutritional source and other gastric juices from the gastrostomy device is prevented by the automatic shut-off valve in the second component.

In a particularly unique embodiment, the first component of the connector includes an elongated body having a first end that is configured for receipt of a feeding tube therein, and a second generally cylindrical end. The second component of the connector has a first end configured for receipt of a feeding adaptor therein and a second end defining a cylindrical recess for receipt of the cylindrical end of the first component. The shut-off valve of the first component is engaged and moved to an open position by a structural member in the second component upon connecting the first and second components together. For example, the shut-off valve in the first component may include a tapered plug member that is moveable within a tapered chamber. The plug member may include a forward-most nub or other structure that extends through an opening in the second end of the first component. This nub is engaged by a structural component in the second end of the second component upon mating the first and second components, resulting in the plug being moved to an open position within the chamber. In this open position, the nutritional solution is free to flow through the first component and into the second component. Upon disconnecting the first and second components the plug member is moved to a sealed position within the chamber by the force of fluid flow through the first component in the first direction.

A unique advantage of the connector is that upon an inadvertent disconnection of the first and second components resulting in automatic closure of the valve in the first component, the nutrition source (e.g., the feed pump) will detect this event as an occlusion or clog in the feed line and set off an appropriate alarm. This alarm notifies the caregiver of an abnormal condition, wherein the connector can be immediately reconnected without significant disruption of the nutritional solution to the patient.

It should be appreciated that other suitable shut-off valves may be used in the first component to accomplish the same function of the tapered plug and chamber, and it is within the scope and spirit of the invention to incorporate any suitable type of shut-off valve.

The shut-off valve in the second component may be any conventional device that functions essentially as a check valve to prevent back flow of nutritional solution and gastric by-products from the gastrostomy device. In this manner, the shut-off valve in the second component may be a valve that is biased to a closed position against flow through the second component in the second direction, and is opened by fluid flow through the second component in the first direction. An example of this type of valve is a resilient flap-type of valve wherein a flap member is opened to fluid flow in a first direction, and is caused to seal against a seat to prevent flow in an opposite second direction. A particular type of resilient-flap valve is known in the art as a "duckbill" valve. Duckbill valves typically have opposed resilient flap members that separate and allow fluid flow in a first direction, and seal against each other to prevent flow in an opposite second direction.

Either or both of the first and second components may further include a clamping mechanism that is configured to releasably clamp the component to its respective feeding device. In a particular embodiment, this clamping mechanism may include a configuration of zip-tie connectors that engage and pull a member of the feeding device, such as a flange, into engagement towards the component. The zip-tie connectors are adjustably secured in a releasable latch. In an alternative embodiment, the clamping mechanism may include a rigid frame structure that is threadedly engaged with the first or second component. The frame engages and pulls the feeding device against the component as the rigid frame is advanced on the component by, for example, a threaded ring member. In still an alternative embodiment, the clamping mechanism on the first or second component may include a compression ring that is threadedly engaged on the component to compress a portion of the component over a portion of the respective feeding device which is fitted to the component.

It should be readily appreciated that the present invention also encompasses any manner of enteral feeding system incorporating the connector according to the invention as set forth herein.

Aspects of the invention will be described in greater detail below by reference to particular embodiments thereof.

DETAILED DESCRIPTION

Reference will now be made in detail to embodiments of the present invention, examples of which are illustrated in the Figs. Each embodiment is provided by way of explanation of the invention, at not meant as a limitation of the invention. For example, features illustrated or described as part of one embodiment may be used with another embodiment to yield still a further embodiment. It is intended that the present invention include these and other modifications and variations coming within the scope and spirit of the invention.

Figure 1:
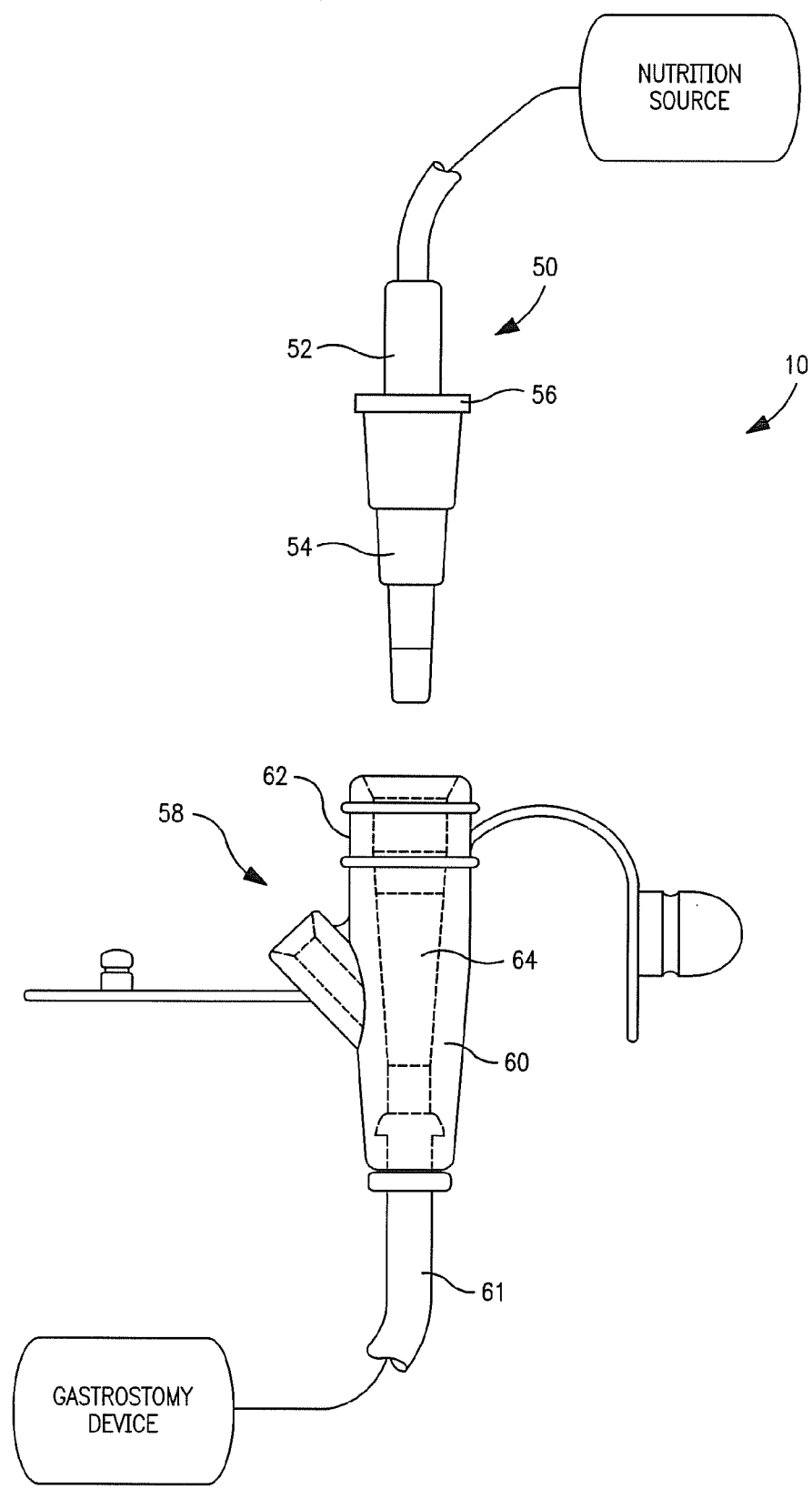
FIG. 1 is partial component view of an exemplary enteral feeding system.

FIG. 1 is a representation of an enteral feeding system 10 that is conventionally utilized to provide nutrition to a patient. The system 10 includes a first feeding device 50 that is in communication with a nutritional solution source. In this particular embodiment, the first feeding device 50 incorporates a feeding tube 52 mated with a connector element 54. Element 54 includes any manner of support structure, such as a flange 56, and may include a stepped-tapered end for engagement into a second feeding device 58. In the illustrated embodiment, the second feeding device 58 is a conventional feeding adaptor 60 having an outer circumferential wall 62 defining an inner stepped channel 64 into which the tapered end of the connector element 54 is inserted. A tube 61 connects the adaptor 60 to a gastrostomy device that is implanted in the patient. The construction and operation of enteral feeding systems incorporating any manner of connectable feeding devices between a nutritional source and a patient gastrostomy device are well known and understood in the art, and a detailed explanation thereof is not necessary for purposes of the present disclosure.

It should also be readily appreciated that the first feeding device 50, and second device 58 illustrated in FIG. 1 are exemplary types of feeding devices that may be used in an enteral feeding system 10, and such devices are not a limitation of the scope and use of a connector in accordance with aspects of the invention.

Figure 2A:
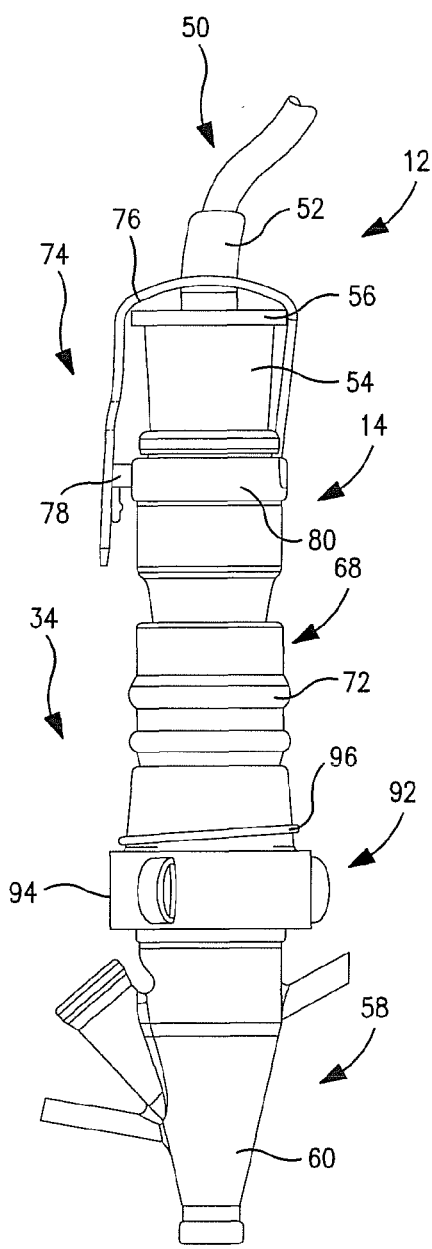
FIG. 2A is a perspective view of an embodiment of a connector in accordance with aspects of the invention for use as an in-line component of an enteral feeding system.
Figure 2B:
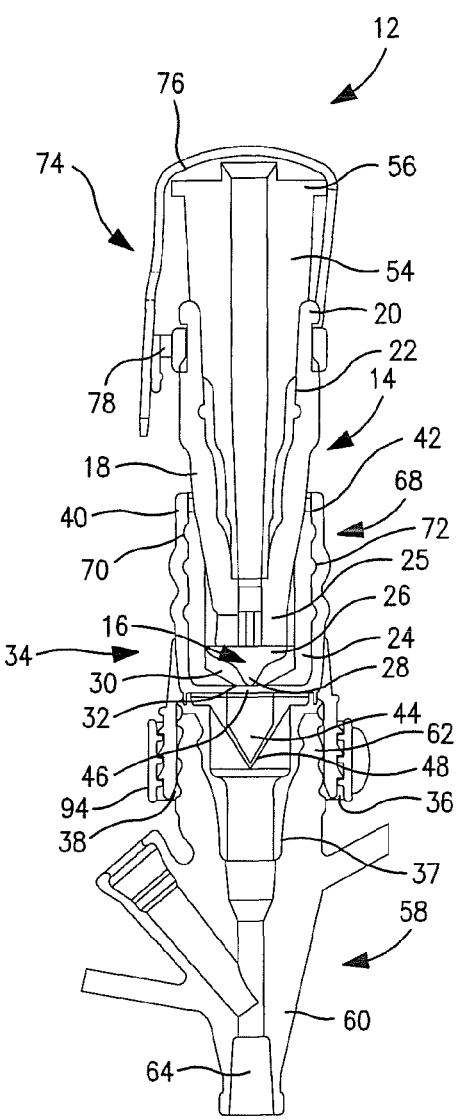
FIG. 2B is a cross-sectional view of the connector of FIG. 2A.
Figure 4:
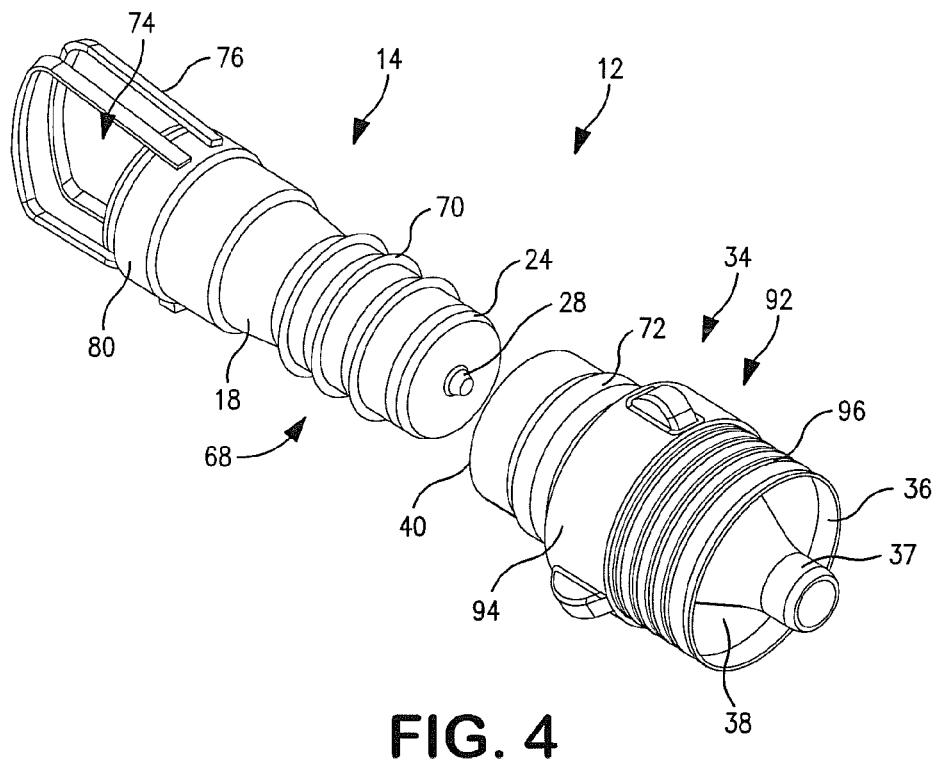
FIG. 4 is a perspective view of the components of the connector of FIGS. 2A and 2B.

FIGS. 2A and 2B illustrate a particular embodiment of a connector 12 in accordance with aspects of the invention. FIG. 4 is a disassembled component view of the connector 12. Referring to FIGS. 2A, 2B, and 4, the connector 12 includes a first component 14 that is connectable to the first feeding device 50, in particular to the connector element 54. The connector 12 includes a second component 34 that is connectable to the second feeding device 58, in particular to the feeding adaptor 60. A releasable coupling, generally 68, is configured between the first component 14 and second component 34. In the illustrated embodiment, this coupling 68 is defined by a detent configuration wherein circular detents 70 provided adjacent to a second end 24 of the first component 14 engage within correspondingly shaped grooves 72 defined within a second end 40 of the second component 34. This detent configuration ensures that the components remain securely connected in operation of the connector 12, yet allow the first and second components to be manually pulled apart. It should be readily appreciated that any manner of conventional releasable coupling devices may be used to connect the first and second components together.

In the connected state of the first component 14 and second component 34 illustrated, for example, in FIG. 2A, the components define a fluid passage between the first feeding device 50 and second feeding device 58.

Each of the first and second components 14, 34, includes an automatic shut-off valve. For example, component 14 includes a shut-off valve 16 that prevents flow of the nutritional solution out of the first component 14 in a first direction. The second component 34 includes a shut-off valve 44 that prevents back flow of nutritional solution and other gastric juices from leaking out of the second component 34 in a disconnected state of the connector 12.

It should be readily appreciated that the individual types of shut-off valves in the first and second components 14, 34, are not limited to the types of valves illustrated and discussed herein. Any number of valves that allow flow in one direction, yet prevent flow in an opposite direction, or only allow fluid flow upon being actuated to an open position, are known in the art and any configuration of such valves may prove useful in the connector 12 according to the present invention.

In the illustrated embodiment, the first component 14 includes an elongated body 18 having a first cylindrical end 20 that is configured for receipt of the first feeding device 50, such as the feeding tube 52 and connector element 54, within a recess 22. The first component 14 may include a second generally cylindrical end 24 that engages within a cylindrical recess 42 defined in a second end 40 of the second component 34 by way of the releasable coupling 68, as discussed above and particularly illustrated in FIG. 2B. The second component 34 includes a first end 36 that engages with the second feeding device 58, in particular with the feeding adaptor 60.

The shut-off valve 44 in the second component 34 may be any conventional type of check valve that allows fluid flow in a first direction, yet prevents flow in an opposite second direction. In the illustrated embodiment, the shut-off valve 44 is defined by a conventional resilient-flap valve referred to in the art as a "duckbill" valve. It should be readily appreciated that any type of check valve may be utilized in this regard.

Referring to FIGS. 2B and 4, the second component 34 includes a recess 38 defined in the first end 36 for receipt of wall 62 of the feeding adaptor 60. A conically shaped tip 37 is concentric within the recess 38 and frictionally engages within the tapered channel 64 within the feeding adaptor 60, as particularly illustrated in FIG. 2B.

Figure 3A:
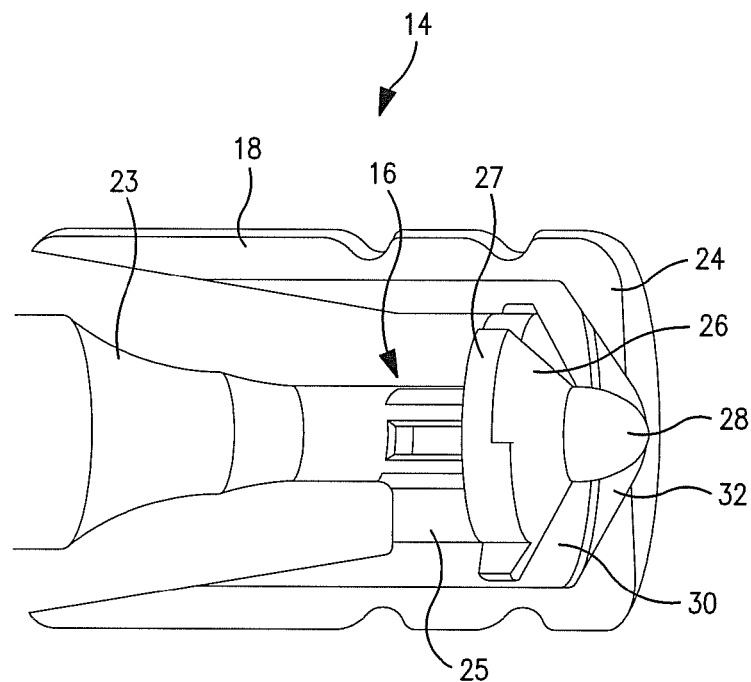
FIGS. 3A and 3B are cross-sectional operational views of a component of the connector of FIGS. 2A and 2B.
Figure 3B:
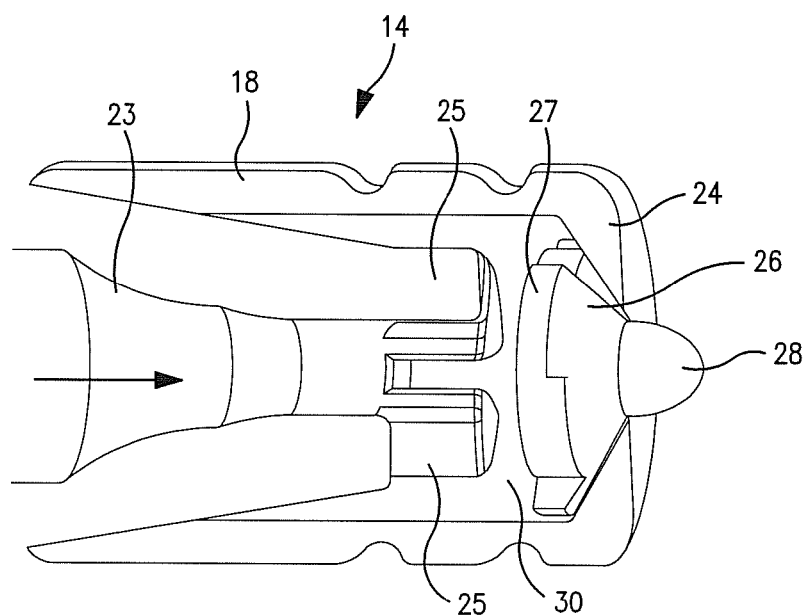

Referring particularly to FIGS. 2B, 3A, and 3B, the shut-off valve 16 in the illustrated embodiment includes a member that is engaged and moved to an open position by engagement of the first component 14 with the second component 34. For example, referring particularly to FIGS. 3A and 3B, the shut-off valve 16 includes a tapered plug member 26 that "floats" within a tapered chamber 30. An opening 32 in the end 24 of the first component 14 provides access out of the chamber 30. The plug member 26 includes a number of circumferentially spaced tabs 27 therearound that provide for alignment and stability of the plug member 26 within the chamber 30. A protruding nub 28 is defined in the center of the tapered plug 26. The nub 28 extends through the opening 32 in a sealed position of the valve 16 as illustrated in FIG. 3B. Fluid flow from the nutritional source is conveyed through the channel 23 in the first component 14 and is directed into the chamber 30 through the circumferentially spaced cage members 25. In a disconnected state of the first component 14, this fluid flow causes the plug 26 to seat against the tapered walls of the chamber 30, thus sealing the opening 32 and preventing the fluid from leaking out of the first component 14. When the first component 14 is engaged into the second component 34, as illustrated in FIG. 2B, a structural component within the second component 34 engages the nub 28 and presses the plug 26 into the chamber 30 against the end of the cage members 25, as illustrated in FIG. 3A. In this position of the tapered plug 26, fluid is free to travel through the channel 23, out through the cage members 25 and into the chamber 30, around the tabs 27 on the plug 26, and out through the opening 32 and into the second component 34. In the illustrated embodiment, the structural element within the second component 34 which engages the nub 28 is a perforated plate member 46. This plate 46 may be, for example, a sieve plate, or any other type of perforated plate that allows fluid flow therethrough. In an alternative embodiment, the engaging component may be a pin or any other type of structure that is positioned to engage the nub 28.

Thus, in summary, in the connected configuration of the first component 14 and second component 34 in the embodiment illustrated in FIGS. 2A and 2B, fluid from the nutritional source is directed through the first feeding device 50 and into the channel 23. The fluid is directed from the channel through the cage members 25 and into the chamber 30. In the engaged configuration of the components 14, 34, the plug 26 is unseated from the tapered walls of the chamber 30 and is backseated against the cage members 25. In this position of the plug 26, fluid is free to travel around the plug and exit through the opening 32. The fluid passes through the sieve or perforations in the engaging plate 46 and through the duckbill valve 44 in the second component 34. The fluid pressure opens the duckbill valve 44, and the nutritional fluid is allowed to pass into the feeding adaptor 58.

In the disconnected state of the components 14, 34, as illustrated in FIG. 4, the duckbill valve 44 prevents backflow leakage of the nutritional fluid and any other gastric juices from the adaptor 58. Positive fluid pressure within the first component 14 causes the tapered plug 26 to assume the sealed position illustrated in FIG. 3B, thus preventing any leakage of the nutritional fluid from the first feeding device 50 through the first component 14. As previously mentioned, closure of the tapered plug 26 upon an inadvertent disconnection of the first and second components may result in an alarm condition at the feed source. This alarm will notify the caregiver of an abnormal condition, wherein the connector can be immediately reconnected without significant disruption of the nutritional solution to the patient.

It may be desirable to include any manner of clamping mechanism with either of the first or second components 14, 34, to insure that the components stay engaged with their respective feeding devices. In the embodiment of FIGS. 2A, 2B, and 4, a clamping mechanism 74 is provided in the form of a zip-tie configuration wherein zip-tie connector elements 76 engage on either side of the feeding tube connector 54, as illustrated in FIG. 2A, and are secured by a releasable clamp 78. The zip-tie elements 76 and latches 78 may be contained on a band 80 that fits onto the first end 20 of the first component 14. The zip-tie elements 76 pull the flange 56 of the connector element 54 into engagement within the recess in the first component 14 and ensure that the connector element 54 cannot be inadvertently pulled from the first component 14.

Figure 5:
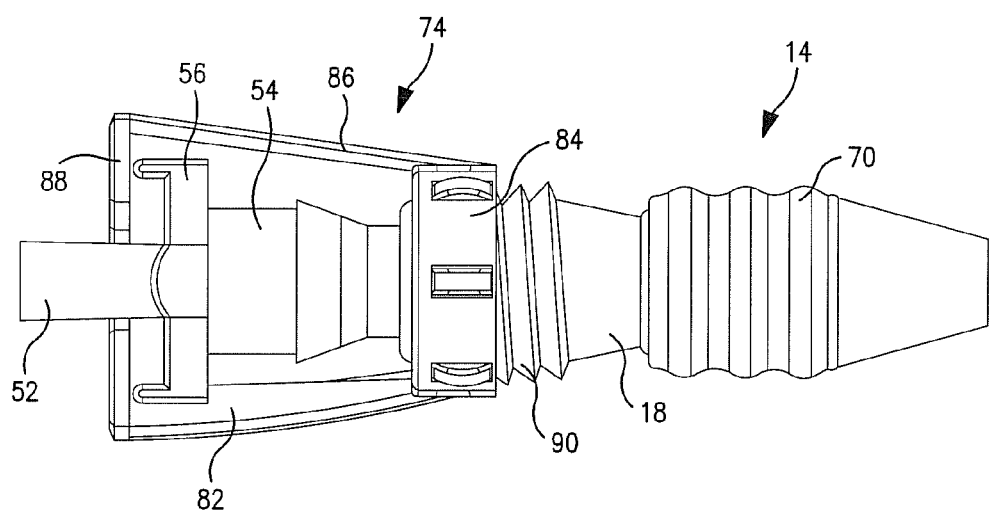
FIG. 5 is a perspective view of an alternate embodiment of a connector for use in an enteral feeding system.

The embodiment of FIG. 5 illustrates a second type of clamping mechanism 74. This mechanism includes a rigid frame structure 82 that is configured on a threaded band 84. The frame 82 includes arms 86 connected to a plate 88 through which the feeding tube 52 extends. The plate 88 engages against a flange 56 or other structure of the connector element 54. The threaded band 84 is axially advanced relative to the elongated body 18 of the first component 14 by rotation of the band 84 on threads 90. Thus, as the band 84 is threadedly rotated towards the second component, the arms 86 and plate 88 pull the connector element 54 into positive engagement within the first component 14.

It may also be desired to include any manner of conventional clamping mechanism on the second component 34. Again, it should be readily appreciated that any manner of conventional connecting or clamping device may be utilized in this regard. In the illustrated embodiment, the second clamping mechanism 92 is a compression ring 94 that is threadedly engaged on body threads 96 of the second component 34, as particularly illustrated in FIG. 2B. Threaded advancement of the compression ring 94 towards the first end 36 of the second component 34 causes the circumferential wall of the component 34 to radially compress onto the circumferential wall 62 of the feeding adaptor 60 that is inserted within the recess 38 in the end of the second component 34. To release the component 34 from the adaptor 60, the compression ring 94 is simply rotated in the opposite direction to release the compressive force.

It should be readily appreciated that the invention also encompasses use of one or more of the connectors 12 in accordance with the invention as an in-line component within any manner of conventional enteral feeding system 10.

It should be appreciated by those skilled in the art that various modifications and variations can be made to the embodiments of the invention illustrated and described herein without departing from the scope and spirit of the invention.

What is claimed is:

1. An in-line connector for use in an enteral feeding system, said connector comprising:
   a first component connectable to a first feeding device of the feeding system, and a second component connectable to a second feeding device of the feeding system;
   a releasable coupling configured between said first and second components, wherein in a connected state said first and second components define a fluid passage between the first and second feeding devices;
   each of said first and second components further comprising an automatic shutoff valve configured therein such that in a disconnected state of said first and second components, said shutoff valve in said first component prevents flow out of said first component in a first direction and said shutoff valve in said second component prevents flow out of said second component in a second direction that is opposite from the first direction;
   said shutoff valve in said first component comprising a tapered plug member that floats within a tapered chamber, said plug member being actuated to a sealed position within said tapered chamber by fluid flow through said first component in the first direction; and
   said shutoff valve in said second component disposed at a location so as to remain biased to a closed position upon full secured connection of said first and second components and to open only upon fluid flow through said second component in the first direction, said shutoff valve in said second component configured to prevent fluid flow opposite the first direction.

2. The in-line connector as in claim 1, wherein said first component comprises an elongated body having a first end configured for receipt of a feeding tube therein, and a second generally cylindrical end, said second component having a first end configured for receipt of a feeding adapter therein and a second end defining a cylindrical recess for receipt of said cylindrical end of said first component, said shutoff valve in said first component being engaged and moved to an open position by a component in said second end of said second component upon connecting said first and second components together.

3. The in-line connector as in claim 2, said plug member further comprising an engagement nub extending through an opening in said second end of said first component, said nub engaged by said component in said second end of said second component to move said plug to an open position of said shutoff valve in said first component.

4. The in-line connector as in claim 1, wherein said shutoff valve in said second component comprises a resilient flap-type valve.

5. The in-line connector as in claim 1, wherein said releasable coupling comprises a detent mechanism configured between surfaces of said first and second components.

6. The in-line connector as in claim 1, further comprising a clamping mechanism on said first component configured to releasably clamp said first component to said first feeding device, said clamping mechanism comprising a connector that engages and pulls a flange on said first feeding device of the feeding system towards said first component.

7. The in-line connector as in claim 1, further comprising a clamping mechanism on said first component configured to releasably clamp said first component to the first feeding device, said clamping mechanism comprising a rigid frame that is threadedly engaged with said first component, said frame engaging and pulling a flange on the first feeding device towards said first component as said frame is threadedly advanced on said first component.

8. The in-line connector as in claim 1, further comprising a clamping mechanism on said second component configured to releasably clamp said second component to the second feeding device, said clamping mechanism comprising a compression ring that is threadedly engaged with said second component to compress a portion thereof over the second feeding device.

9. An in-line connector for use in an enteral feeding system, said connector comprising:
   a first component having an elongated body with a first end configured for receipt of a feeding tube therein, and a second end;
   a second component having a first end configured for receipt of a feeding adapter therein and a second end defining a recess for receipt of said first end of said first component;
   a releasable coupling configured between said first and second components, wherein in a connected state said first and second components define a fluid passage between the feeding tube and feeding adapter;
   each of said first and second components further comprising an automatic shutoff valve configured therein such that in a disconnected state of said first and second components, said shutoff valve in said first component prevents flow out of said first component in a first direction and said shutoff valve in said second component prevents flow out of said second component in a second direction that is opposite from the first direction;

said shutoff valve in said first component being engaged and moved to an open position by a component in said second end of said second component upon full secured connection of said first and second components together; and said shutoff valve in said second component disposed at a location so as to remain biased to a closed position in the full secured connection state of said first and second components, and is opened by fluid flow through said second component in the first direction, said shutoff valve in said second component configured to prevent fluid flow opposite the first direction.

10. The in-line connector as in claim 9, wherein said shutoff valve in said first component comprises a tapered plug member movable within a tapered chamber, said plug member further comprising an engagement nub extending through an opening in said second end of said first component, said nub engaged by said component in said second end of said second component to move said plug to an open position of said shutoff valve in said first component.

11. The in-line connector as in claim 9, wherein said shutoff valve in said second component comprises a resilient flap-type valve.

12. The in-line connector as in claim 9, further comprising a clamping mechanism on said first component configured to releasably clamp said first component to the feeding tube, and a clamping mechanism on said second component configured to releasably clamp said second component to the feeding adapter.

13. An enteral feeding system for delivering a nutritional solution to a gastrostomy feeding device in a patient, said system comprising:

an upstream feeding device, and a downstream feeding device;

an in-line connector configured between said upstream and downstream feeding devices, said connector further comprising:

a first component connectable to said upstream feeding device, and a second component connectable to said downstream feeding device;

a releasable coupling configured between said first and second components, wherein in a connected state said first and second components define a fluid passage between the upstream and downstream feeding devices;

each of said first and second components further comprising an automatic shutoff valve configured therein such that in a disconnected state of said first and second components, said shutoff valve in said first component prevents flow out of said first component in a first direction and said shutoff valve in said second component prevents flow out of said second component in a second direction that is opposite from the first direction;

said shutoff valve in said first component being engaged and moved to an open position by said second component upon full secured connection of said first and second components together; and said shutoff valve in said second component disposed at a location so as to remain biased to a closed position against flow through said second component in the full secured connection state of said first and second components, and is opened by fluid flow through said second component in the first direction, said shutoff valve in said second component configured to prevent fluid flow opposite the first direction.

14. The feeding system as in claim 13, wherein said upstream feeding device comprises a feeding tube and said downstream feeding device comprises a feeding adapter, said first component comprising an elongated body having a first end configured for receipt of said feeding tube therein, and a second generally cylindrical end, said second component having a first end configured for receipt of said feeding adapter therein and a second end defining a cylindrical recess for receipt of said cylindrical end of said first component.

15. The feeding system as in claim 14, wherein said shutoff valve in said first component comprises a tapered plug member movable within a tapered chamber, said plug member further comprising an engagement nub extending through an opening in said second end of said first component, said nub engaged by a component in said second end of said second component to move said plug to an open position of said shutoff valve in said first component.

16. The feeding system as in claim 15, wherein said plug member is moved to a sealed position within said chamber by fluid flow through said first component in the first direction.

17. The feeding system as in claim 13, wherein said releasable coupling comprises a detent mechanism configured between surfaces of said first and second components.

18. The feeding system as in claim 13, further comprising a clamping mechanism on said first component configured to releasably clamp said first component to said upstream feeding device, said clamping mechanism comprising a zip-tie connector that engages and pulls a flange on said upstream feeding device towards said first component.

19. The feeding system as in claim 13, further comprising a clamping mechanism on said first component configured to releasably clamp said first component to said upstream feeding device, said clamping mechanism comprising a rigid frame that is threadedly engaged with said first component, said frame engaging and pulling a flange on said upstream feeding device towards said first component as said frame is threadedly advanced on said first component.

20. The feeding system as in claim 13, further comprising a clamping mechanism on said second component configured to releasably clamp said second component to said downstream feeding device, said clamping mechanism comprising a compression ring that is threadedly engaged with said second component to compress a portion thereof over said downstream feeding device.

* * * * *